United States Patent
Ahonen et al.

(10) Patent No.: US 10,315,053 B2
(45) Date of Patent: Jun. 11, 2019

(54) RADIATION TREATMENT PLATFORM AND METHOD USING A PORTAL IMAGING DEVICE TO AUTOMATICALLY CONTROL THERAPY ADMINISTRATION

(71) Applicant: Varian Medical Systems International AG, Cham (CH)

(72) Inventors: Risto Ahonen, Espoo (FI); Esa Kuusela, Espoo (FI); Tuomas E. Torsti, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 0 days.

(21) Appl. No.: 16/055,491

(22) Filed: Aug. 6, 2018

(65) Prior Publication Data

US 2019/0022419 A1    Jan. 24, 2019

Related U.S. Application Data

(63) Continuation of application No. 15/086,530, filed on Mar. 31, 2016, now abandoned.

(51) Int. Cl.
*A61N 5/10* (2006.01)
(52) U.S. Cl.
CPC ......... *A61N 5/1071* (2013.01); *A61N 5/1048* (2013.01); *A61N 5/1067* (2013.01); *A61N 5/1081* (2013.01); *A61N 2005/1054* (2013.01); *A61N 2005/1072* (2013.01)

(58) Field of Classification Search
CPC .. A61N 5/1049; A61N 5/1064; A61N 5/1071; A61N 2005/1074; A61N 2005/1092; A61N 5/10; A61N 5/103; A61N 2005/1081
See application file for complete search history.

(56) References Cited

U.S. PATENT DOCUMENTS

| | | | |
|---|---|---|---|
| 9,265,971 B2 | 2/2016 | Baltes et al. | |
| 9,314,160 B2 | 4/2016 | Adler, Jr. et al. | |
| 2010/0176309 A1* | 7/2010 | Mackie | A61N 5/10 250/492.3 |
| 2013/0329856 A1 | 12/2013 | Kuwahara et al. | |

FOREIGN PATENT DOCUMENTS

EP     2904974 A1    8/2015

OTHER PUBLICATIONS

PCT Search Report and Written Opinion dated Jul. 21, 2017 from International Application No. PCT/IB2017/000463; 16 pages.

* cited by examiner

*Primary Examiner* — Don K Wong
(74) *Attorney, Agent, or Firm* — Fitch, Even, Tabin & Flannery LLP

(57) ABSTRACT

A portal imaging device is used to determine an amount of radiation that is delivered to at least one point while administering a radiation treatment therapy to a patient. Upon detecting that the amount of radiation that is delivered to that at least one point exceeds a predetermined amount of radiation (for example, a planned amount of radiation per the radiation treatment plan), administration of radiation treatment therapy to the patient can be automatically halted.

12 Claims, 4 Drawing Sheets

RADIATION TREATMENT PLATFORM AND METHOD USING A PORTAL IMAGING DEVICE TO AUTOMATICALLY CONTROL THERAPY ADMINISTRATION

CROSS-REFERENCE TO RELATED APPLICATION

This application is a continuation of prior U.S. patent application Ser. No. 15/086,530, filed Mar. 31, 2016 which is hereby incorporated herein by reference in its entirety.

TECHNICAL FIELD

These teachings relate generally to radiation treatment platforms including, in particular, portal imaging devices.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use ("optimization" referring to improving upon a candidate treatment plan without necessarily ensuring that the optimized result is, in fact, the singular best solution). Generally speaking, a well-conceived radiation-treatment plan serves to help ensure that the treatment target receives a prescribed dose of radiation while avoiding, to as large an extent as might be possible, undue dosing of surrounding or intervening tissues and organs.

Unfortunately, it can be very difficult for a treatment plan to comprehensively anticipate all possibilities within the dynamic context of a radiation treatment session. As a result, it is possible for a larger-than-intended radiation dose to occur. A less-than-intended radiation dose can be effectively remediated by simply applying additional dosing. It is not possible, however, to take back radiation following administration of a larger-than-intended radiation dose.

BRIEF DESCRIPTION OF THE DRAWINGS

The above needs are at least partially met through provision of the radiation treatment platform and method using a portal imaging device to automatically control therapy administration described in the following detailed description, particularly when studied in conjunction with the drawings, wherein.

Figure 1:
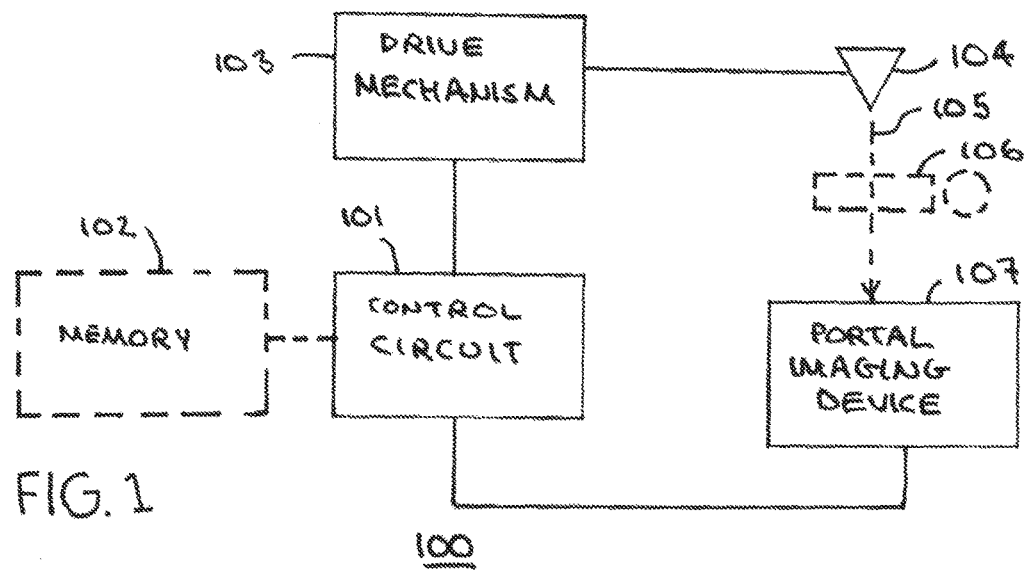
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments make use of a portal imaging device to determine an amount of radiation that is delivered to at least one point while administering a radiation treatment therapy to a patient. Upon detecting that the amount of radiation that is delivered to that at least one point exceeds a predetermined amount of radiation (for example, a planned amount of radiation per the radiation treatment plan), administration of radiation treatment therapy to the patient can be automatically halted.

By one approach the portal imaging device is used to determine an amount that is delivered to each of a plurality of points. In this case, the treatment therapy can be automatically halted when any of these points (or at least some predetermined number of these points) receives an amount of radiation that exceeds a predetermined amount of radiation for such points. By one approach, each monitored point can have a separately-determined (and hence potentially different) predetermined amount of radiation applicable thereto.

By one approach the monitored radiation at the point of interest (or points of interest) comprises an aggregated amount of radiation that is delivered to such a point over time during the treatment session (or even over multiple treatment sessions if desired).

If desired, the monitored point does not constitute a point within a patient volume. Instead, the monitored point can comprise a point that is external to the patient. In such a case the aforementioned predetermined amount of radiation does not constitute a calculated dose that corresponds to a volume in the patient but instead constitutes a calculated dose for a point external to the patient. As one illustrative example in these regards the monitored point comprises a point on a virtual cylinder that is disposed about but that does not include the patient.

So configured, a portal imaging device is repurposed to serve in other than its ordinary regards. Pursuant to these teachings a radiation treatment can be automatically halted when an overdosing (or a potential overdosing) condition occurs.

These and other benefits may become clearer upon making a thorough review and study of the following detailed description. Referring now to the drawings, and in particular to FIG. 1, an illustrative apparatus 100 that is compatible with many of these teachings will be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one optional approach the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to a radiation treatment plan, one or more predetermined radiation thresholds, and so forth, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In this illustrative example the control circuit 101 also operably couples to a drive mechanism 103 for a movable radiation source 104. This radiation source 104 can be configured to move (in response to the drive mechanism 103) with respect to a patient 106 who rests, for example, atop a patient-support surface such as a couch (not shown in this figure). For example, the radiation source 104 can be mounted to a gantry (not shown) that circumscribes a full circle or less than a full circle about the patient 106. So configured, the radiation source 104 can move (continuously or intermittently as desired) about the patient 106 during a given treatment session to thereby direct a radiation beam 105 towards a treatment volume within the patient 106 from a variety of treatment angles. Such movable radiation sources 104 are well known in the art and require no further elaboration here.

Also in this illustrative example a portal imaging device 107 is disposed opposite the radiation source 104 and is also configured to move in conjunction with the movable radiation source 104. Portal imaging devices are known in the art and typically serve to provide a so-called beam's eye view that is used when planning or when evaluating a radiation therapy treatment by, for example, helping to ensure that the relative orientation of the patient and the treatment machine are correct. Portal imaging devices are known in the art and typically employ digital imaging (using, for example, an amorphous silicon flat-panel detector) to create a good quality digital image to facilitate a corresponding quality review. For the sake of an illustrative example it will be presumed here that the portal imaging device 107 comprises a flat-panel detector as is known in the art.

To be clear, although portal imaging devices are known in the art, the use of a portal imaging device as described herein is unusual and represents a repurposing of such a device.

This portal imaging device 107 operably couples to the control circuit 101 and can provide, for example, its imaging output to the control circuit 101 for automated analysis and subsequent use as described herein.

Figure 2:
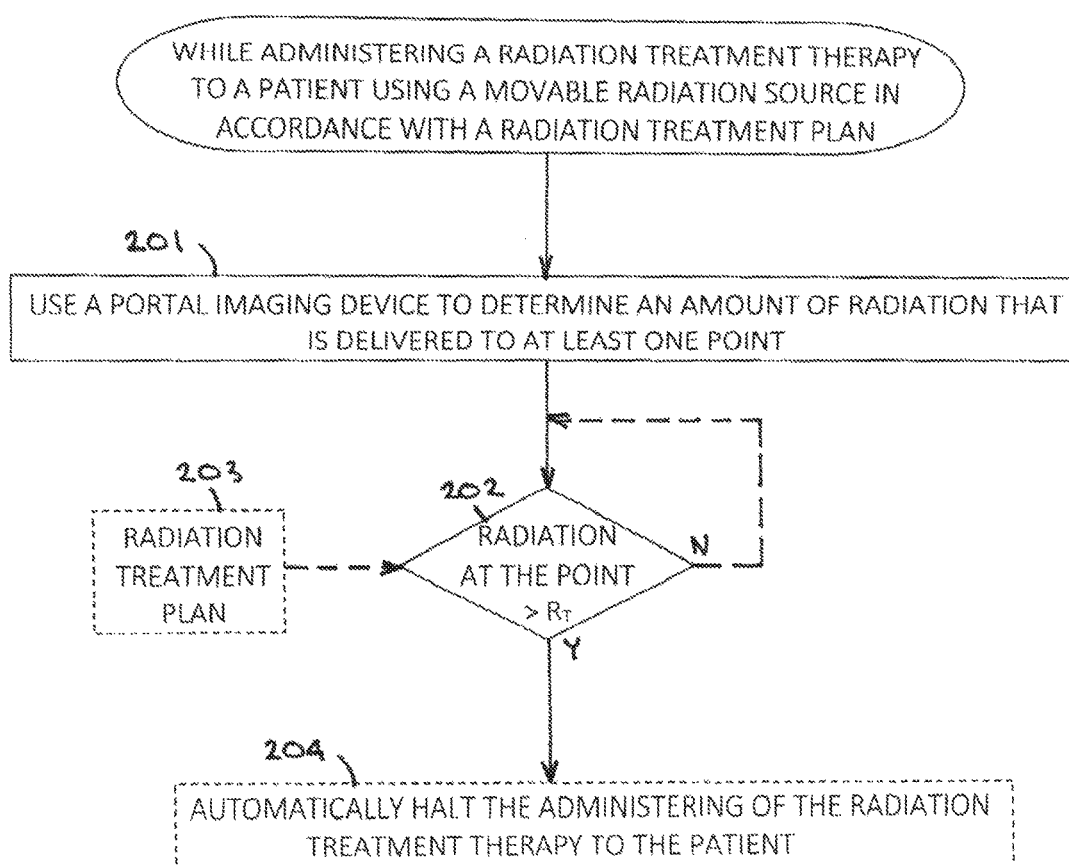
FIG. 2 comprises a flow diagram as configured in accordance with various embodiments of these teachings.

Referring now to FIG. 2, a process 200 that can be carried out while using such an apparatus 100 while administering a radiation treatment therapy to a patient 106 using the movable radiation source 104 in accordance with a radiation treatment plan will be described.

At block 201 this process 200 provides for using the portal imaging device 107 to determine the amount of radiation being delivered to at least one point. To be clear, this occurs during the administration of the radiation treatment therapy to the patient 106 and hence comprises a non-traditional use of a portal imaging device 107. By one approach the foregoing occurs on a fully or at least a largely continuous basis while the radiation treatment therapy is administered to the patient 106. These teachings will accommodate other approaches in these regards, however, such as intermittent monitoring on a periodic or episodic basis.

In a typical application setting it can be useful to make the foregoing determination for a plurality of such points. That is, block 201 can comprise using the portal imaging device 107 to determine an amount of radiation that is delivered to each of a plurality of points.

Figure 3:
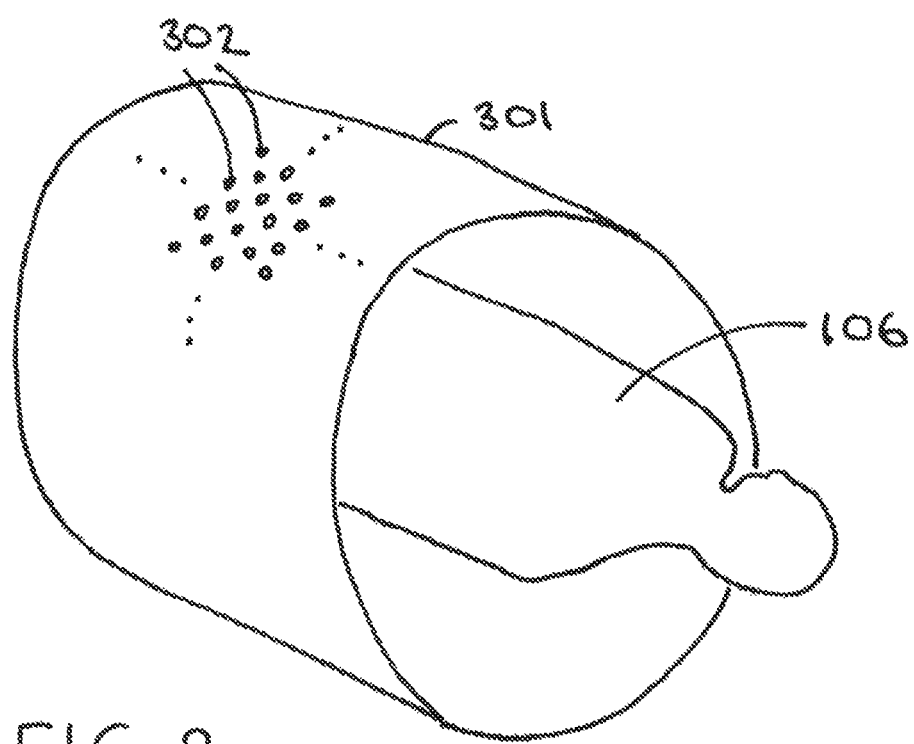
FIG. 3 comprises a perspective schematic view as configured in accordance with various embodiments of these teachings.

By one approach the patient 106 includes the monitored point. By another approach, however, one or more of the monitored points does not correspond to a volume in the patient. FIG. 3 provides one illustrative example in these regards. In this example, a plurality of the monitored points 302 comprise points on a virtual cylinder 301 that is disposed about but that does not include the patient 106. In such a case the points 302 can be regularly spaced apart from one another pursuant to some pattern of choice. In any event, the points 302 can be densely packed or generously spaced apart from one another, and as evenly spaced or unevenly spaced, as desired. These teachings will also accommodate, if desired, permitting adjacent points to overlap one another somewhat or to prohibit any overlapping at all.

At block 202 this process 200 provides for detecting when the amount of radiation that is delivered to the at least one point (or to any of the points when a plurality of such points are monitored) exceeds a predetermined amount of radiation (denoted here by $R_T$). By one optional approach the predetermined amount of radiation $R_T$ comprises a planned amount of radiation per the aforementioned radiation treatment plan 203. For example, the predetermined amount of radiation $R_T$ can comprise a predicted level of radiation that is expected at this point at some particular time during the execution of the radiation treatment plan 203. When monitoring such a point or points over time, this block 202 can comprise detecting when an aggregated (i.e., accumulated) amount of radiation that is delivered to one or more of the plurality of points exceeds the predetermined amount of radiation $R_T$.

When monitoring a point that does not correspond to a volume in the patient 106, such as when monitoring a point on the aforementioned virtual cylinder 301, it should be noted that the relevant predetermined amount of radiation $R_T$ does not constitute a calculated dose that corresponds to a volume in the patient 106. Instead, the predetermined amount of radiation $R_T$ comprises a calculated amount for that particular point (such as, for example, a particular point 302 on the aforementioned virtual cylinder 301).

Figure 4:
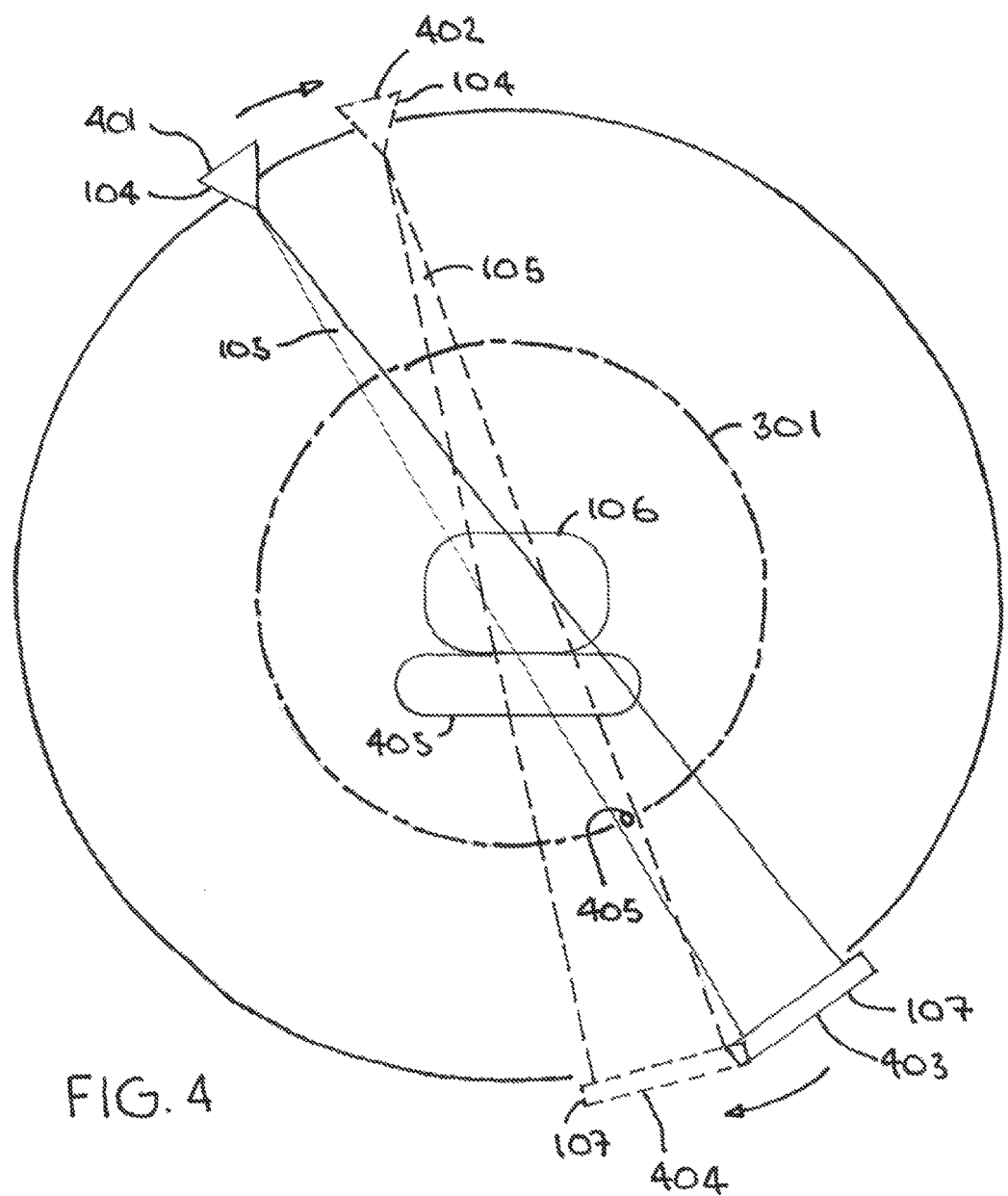
FIG. 4 comprises a side-elevational schematic view as configured in accordance with various embodiments of these teachings.

As noted above, these teachings can provide for detecting when an aggregate amount of radiation that is delivered to a particular point exceeds a predetermined amount of radiation $R_T$. By one approach this can comprise detecting when the aggregate amount of radiation that is delivered to the monitored point while the movable radiation source 104 is at different locations exceeds a corresponding predetermined amount of radiation. FIG. 4 provides an illustrative example in these regards.

In this example a patient 106 lies atop a couch 405 and the movable radiation source 104 is able to move via a gantry (not shown) in an arcuate manner as shown about the patient 106. The portal imaging device 107 is located opposite the movable radiation source 104 on the other side of the patient 106 and moves as the radiation source 104 moves. This figure also illustrates the aforementioned virtual cylinder 301 with one particular monitored point on that virtual cylinder 301 being denoted by reference numeral 405.

When the movable radiation source 104 is at a first position (denoted by reference numeral 401) and the portal imaging device 107 is at a corresponding opposing position denoted by reference numeral 403, the corresponding radiation beam 105 includes the aforementioned monitored point 405. Accordingly, radiation delivered to that monitored point 405 is detected and quantified by the portal imaging device 107 when the radiation source 104 is at this first position 401.

Similarly, when the movable radiation source 104 moves to a second position (denoted by reference 402) and the portal imaging device 107 is at a corresponding opposing position denoted by reference 404, the corresponding radiation beam 105 again includes the aforementioned monitored point 405. So again, radiation delivered to that monitored point 405 is detected and quantified by the portal imaging device 107. Accordingly, the readings of the portal imaging device 107 can be reliably aggregated for this particular monitored point 405 while the movable radiation source 104 is at these different locations. (It will be understood that the portal imaging device 107 can be similarly employed to gather information regarding the amount of radiation that is delivered to this point 405 while the movable radiation source 104 moves between these two locations 401 and 402 when the radiation source 104 continuously emits the radiation beam 105 while so moving.)

Using such an approach, and viewing the overall arc traversed by the radiation source 104 as an arc field, the accumulated radiation dose at each point of interest can be calculated for each of a sequence of sampled sub-arc fields. The actual aggregated dose at each such sub-arc field can then be compared against the calculated amount for the corresponding sub-arc field to determine whether an overdosing is occurring (or is about to occur).

When monitoring a point that does not correspond to a volume in the patient 106, the predetermined amount of radiation $R_T$ will likewise typically not constitute a calculated dose that corresponds directly to a volume in the patient 106 but will instead comprise a calculated, predicted amount for the point in question (such as the aforementioned point 405 on the virtual cylinder 301). That said, this calculated amount for a point that is not within the patient 106 can nevertheless comprise an amount that is calculated per the radiation treatment plan 203 if desired. Accordingly, the radiation delivered to such a point can nevertheless provide a reliable indication of the radiation dosing being received by the patient.

These teachings will support responding in any of a variety of ways to detecting an overdose at one or more monitored points as described above. By one approach, and as illustrated in FIG. 2, at optional block 204 this process 200 can provide for automatically halting the current administration of the radiation treatment therapy to the patient 106. Such an action can include notifying or otherwise alerting the attending technician(s) that the therapy has been halted if desired.

So configured, these teachings leverage a portal imaging device for purposes other than assessing or assuring the quality of a treatment plan prior to administering that plan. Instead, these teachings use such a device to assess (essentially in real time during administration of a given treatment plan) whether, when, and where a patient is subjected to radiation overdosing.

Those skilled in the art will recognize that these teachings are similarly applicable in application settings where the radiation source remains stationary rather than moving. It will also be understood and appreciated that the above-mentioned aggregated values (either as predicted or as read) can represent multiple treatment sessions as well as a single session or sub-session as desired.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
    while administering a radiation treatment therapy to a patient using a movable radiation source in accordance with a radiation treatment plan, using a portal imaging device to determine an amount of radiation that is delivered to each of a plurality of points on a virtual cylinder that is disposed about but that does not include the patient;
    detecting an excess amount of radiation by at least one of: detecting when the amount of radiation that is delivered to any of the plurality of points exceeds a predetermined amount of radiation for any one of the plurality of points; and detecting when an aggregate amount of radiation that is delivered to at least some of the plurality of points exceeds the predetermined amount of radiation;
    upon detecting the excess amount of radiation, automatically halting the administering of the radiation treatment therapy to the patient.

2. The method of claim 1 wherein the predetermined amount of radiation comprises a planned amount of radiation per the radiation treatment plan.

3. The method of claim 1 wherein using the portal imaging device to determine an amount of radiation that is delivered to each of the plurality of points on the virtual cylinder comprises continuously using the portal imaging device to determine the amount of radiation that is delivered to each of the plurality of points during the radiation treatment therapy.

4. The method of claim 2 wherein detecting the excess amount of radiation comprises detecting when an aggregated amount of radiation that is delivered with respect to the plurality of points while the movable radiation source is at different locations exceeds the predetermined amount of radiation.

5. The method of claim 4 wherein the predetermined amount of radiation does not constitute a calculated dose corresponding to a volume in the patient.

6. The method of claim 5 wherein the predetermined amount of radiation comprises a calculated amount corresponding to the plurality of points on the virtual cylinder.

7. An apparatus comprising:
a movable radiation source;
a drive mechanism configured to selectively move the movable radiation source;
a portal imaging device configured to move in conjunction with the movable radiation source;
a control circuit operably coupled to the portal imaging device and to the movable radiation source and configured to:
while administering a radiation treatment therapy to a patient using the movable radiation source in accordance with a radiation treatment plan, using the portal imaging device to determine an amount of radiation that is delivered to each of a plurality of points on a virtual cylinder that is disposed about but that does not include the patient;
detect an excess amount of radiation by at least one of: detecting when the amount of radiation that is delivered to any of the plurality of points exceeds a predetermined amount of radiation for any one of the plurality of points; and detecting when an aggregate amount of radiation that is delivered to at least some of the plurality of points exceeds the predetermined amount of radiation;
upon detecting the excess amount of radiation, automatically halt the drive mechanism.

8. The apparatus of claim 7 wherein the predetermined amount of radiation comprises a planned amount of radiation per the radiation treatment plan.

9. The apparatus of claim 7 wherein the control circuit is configured to use the portal imaging device to determine an amount of radiation that is delivered to each of the plurality of points on the virtual cylinder by continuously using the portal imaging device to determine the amount of radiation that is delivered to each of the plurality of points during the radiation treatment therapy.

10. The apparatus of claim 8 wherein the control circuit is configured to detect the excess amount of radiation by detecting when an aggregated amount of radiation that is delivered with respect to the plurality of points while the movable radiation source is at different locations exceeds the predetermined amount of radiation.

11. The apparatus of claim 10 wherein the predetermined amount of radiation does not constitute a calculated dose corresponding to a volume in the patient.

12. The apparatus of claim 11 wherein the predetermined amount of radiation comprises a calculated amount corresponding to the plurality of points on the virtual cylinder.

* * * * *